(12) United States Patent
Malawey et al.

(10) Patent No.: US 11,076,803 B2
(45) Date of Patent: Aug. 3, 2021

(54) PASSIVE MULTIPLE FOOT SENSOR INSOLE REAL-TIME FEEDBACK DEVICE

(71) Applicants: Michael J. Malawey, Brentwood, TN (US); Thomas H. Lupfer, San Diego, CA (US); Patrick M. Steusloff, San Diego, CA (US); Thomas A. Liguori, San Diego, CA (US); Michael A. Kurtz, San Diego, CA (US); Michael J. Thilenius, San Diego, CA (US)

(72) Inventors: Michael J. Malawey, Brentwood, TN (US); Thomas H. Lupfer, San Diego, CA (US); Patrick M. Steusloff, San Diego, CA (US); Thomas A. Liguori, San Diego, CA (US); Michael A. Kurtz, San Diego, CA (US); Michael J. Thilenius, San Diego, CA (US)

(73) Assignee: Rehabit Health, LLC, San Diego, CA (US)

( * ) Notice: Subject to any disclaimer, the term of this patent is extended or adjusted under 35 U.S.C. 154(b) by 0 days.

(21) Appl. No.: 15/981,888

(22) Filed: May 16, 2018

(65) Prior Publication Data
US 2021/0022666 A1    Jan. 28, 2021

Related U.S. Application Data

(63) Continuation-in-part of application No. 15/598,277, filed on May 17, 2017, now Pat. No. 10,159,427.

(51) Int. Cl.
| | | |
|---|---|---|
| *G08B 1/08* | (2006.01) | |
| *A61B 5/00* | (2006.01) | |
| *G01L 1/18* | (2006.01) | |
| *G01L 5/00* | (2006.01) | |
| *A61B 5/103* | (2006.01) | |
| *H04M 1/72412* | (2021.01) | |
| *A61H 3/04* | (2006.01) | |
| *A61B 50/26* | (2016.01) | |
| *A45B 3/00* | (2006.01) | |

(52) U.S. Cl.
CPC ............ *A61B 5/486* (2013.01); *A61B 5/0004* (2013.01); *A61B 5/1038* (2013.01); *A61B 5/6807* (2013.01); *A61B 5/742* (2013.01); *A61B 5/7405* (2013.01); *A61B 5/7455* (2013.01); *G01L 1/18* (2013.01); *G01L 5/0052* (2013.01); *H04M 1/72412* (2021.01); *A45B 3/00* (2013.01); *A61B 50/26* (2016.02); *A61H 3/04* (2013.01); *H04M 2250/12* (2013.01)

(58) Field of Classification Search
CPC ....... G06F 15/00; G06F 3/016; A61B 5/1038; A61B 5/112; A61B 5/6807; A63B 2071/0655
See application file for complete search history.

(56) References Cited

U.S. PATENT DOCUMENTS

| | | |
|---|---|---|
| 7,191,644 B2 | 3/2007 | Haselhurst et al. |
| 8,844,166 B2 | 9/2014 | Jazdanian |
| | (Continued) | |

*Primary Examiner* — Toan N Pham
(74) *Attorney, Agent, or Firm* — William Propp, Esq.

(57) ABSTRACT

A foot sensor feedback device with multiple passive sensors in a shoe insole to provide real time feedback for a microprocessor to control a haptic device on the ankle of a person and to store and display data on an application on a smart phone to provide balance to a person while standing still or walking.

13 Claims, 8 Drawing Sheets

(56) References Cited

U.S. PATENT DOCUMENTS

| | | | |
|---|---|---|---|
| 9,113,823 B2 | 8/2015 | Yuen et al. | |
| 9,114,296 B2 | 8/2015 | Reynolds, III | |
| 9,279,734 B2 * | 3/2016 | Walker | G01L 1/18 |
| 9,565,286 B2 | 2/2017 | Chung et al. | |
| 9,591,993 B2 * | 3/2017 | Morris Bamberg | A61B 5/486 |
| 9,743,861 B2 * | 8/2017 | Giedwoyn | G16H 20/30 |
| 2010/0152619 A1 * | 6/2010 | Kalpaxis | A61B 5/1038 |
| | | | 600/592 |
| 2012/0291564 A1 * | 11/2012 | Amos | A43B 3/0005 |
| | | | 73/862.045 |
| 2013/0041617 A1 | 2/2013 | Pease et al. | |
| 2015/0257679 A1 | 9/2015 | Ross | |
| 2016/0345865 A1 * | 12/2016 | Agrawal | G06Q 10/06311 |

\* cited by examiner

PASSIVE MULTIPLE FOOT SENSOR INSOLE REAL-TIME FEEDBACK DEVICE

CROSS-REFERENCE TO RELATED APPLICATIONS

This application is a Continuation in Part of U.S. patent application Ser. No. 15/598,277, filed on May 17, 2017, which is herein incorporated by reference.

BACKGROUND OF THE INVENTION

This invention relates generally to a foot sensor feedback device and, more particularly, this invention is directed to a foot sensor feedback device with multiple passive sensors in a shoe insole to provide real time feedback for a microprocessor to control a haptic device on the ankle of a person and to store and display data on an application on a smart phone to provide balance to a person while standing still or walking.

The walking pattern or gait of a person is the movement of the limbs of the person, especially the legs of the person. The gait can be measured by body weight, center of body mass over the foot, number of steps in the gait cycle, cadence (speed of walking), and/or linear distance while walking.

A person who has suffered a stroke or a leg injury has to undergo rehabilitation to improve and regain a normal walking pattern or gait.

A stroke is a brain injury that can affect the ability of a person to feel parts of his/her body. A stroke occurs when blood supply to the brain is obstructed, causing an oxygen deprivation that kills brain cells, often leaving the victim with only partial brain function. This results in lost neural pathways, which typically impairs the motor skills for one half of the body. A stroke victim often needs to relearn how to use his/her body by rebuilding neural pathways. One of the most difficult tasks to relearn is walking.

The key behind walking rehabilitation for stroke patients is constant repetition. This enables them to eventually learn how to adjust their steps to properly distribute their weight. Stroke victims lack feeling in half of their body due to the lost neural pathways; thus, it is difficult for them to sense how distribute their weight on their feet. It becomes the physical therapist's job to guide the adjustments needed for each step. The process is further challenged by the fact that a fall can result in serious injury. Patients often attempt to walk as they had prior to their stroke, resulting in immediate loss of balance and eventually an incorrect walking gait. Other patients are reluctant to attempt to walk because they do not trust their limbs.

It is possible, with the correct therapy, for a stroke victim to relearn how to walk. However, this feat can take many physically exhausting years for the patient and also the physical therapist.

In observing their physical therapy sessions, the patient will typically be seen with their head down staring at their feet. This is due to the lack of trust they have in themselves and their bodies. Unfortunately, this behavior further harms their posture and balance.

A patient needs to properly load each step and have proper balance. It is crucial that the patient relearns to walk correctly or the chances of walking autonomously in the future are significantly hindered.

Currently, stroke rehabilitation is almost entirely through physical therapy sessions. Repetition of movement is key to rebuild the neural pathways lost in a stroke. However, it is not feasible for stroke victims to pay for daily physical therapy sessions; nor is it feasible for a physical therapist to constantly tend to a single patient.

In order to reduce walking rehabilitation time, stroke victims need a way to practice walking outside of therapy sessions. To do this, stroke victims need a system that can provide assurance that they have the proper step, balance and posture with their target foot, which is the role a physical therapist takes during sessions.

Some solutions to the problem offer complex mechanical designs, but these provide physical support for the leg rather than the type of feedback that can help a patient learn to perform the walking motion autonomously.

In addition to neurological stroke patients, physically injured leg patients also need to undergo rehabilitation to improve and regain a normal walking pattern or gait. The physical injuries can include breaking or bruising one or more leg bones, straining or tearing one or more leg muscles, realignment of bones and/or muscles, and generally weakened bones and/or muscles.

With the advanced capabilities of sensors and microprocessors currently available, there are many rehabilitation options to explore. The opportunity arises for a "smart" insole, utilizing sensors, wireless communication, and various forms of feedback to enable in-home therapy. By having the means to work with a familiar caretaker at home, stroke victims will be able to put in the needed repetition more often than before, while still receiving careful guidance.

A lower leg sensor device provides real time data about a person's walking or running in U.S. Pat. No. 9,114,296. The lower leg sensor device has a position angle sensor on the lower leg and a foot contact sensor. The sensors provide data on the angle of the lower leg and the line of gravity.

However, angle position of the leg to determine a walking pattern is not as effective as using the foot itself, specifically the body weight on the sole of the foot, to determine the walking pattern. Similarly, the measurement of the multiple factors of the walking pattern on the sole of the foot—body weight, center of body mass over the foot, number of steps in the gait cycle, cadence (speed of walking), and/or linear distance—is more effective than a single factor of the angle of the leg.

A portable activity monitoring device to calculate activity points of a person corresponding to physical activity of the person having an altitude sensor, a heart rate sensor and a motion sensor in a housing is in U.S. Pat. No. 9,113,823.

However, the patent invention is mounted on the foot, not under the sole.

The patent has additional sensors in additional body locations, rather than sensors on just the sole.

Again, the measurement of the multiple factors of the walking pattern on the sole of the foot—body weight, center of body mass over the foot, number of steps in the gait cycle, cadence (speed of walking), and/or linear distance—is more effective than measuring factors on the foot, not the sole of the foot.

The patent does not disclose an app or the explicit use of a smartphone.

A gyroscopic sensor under the foot of the person transmits angular velocity data to a remote person feedback device which emits a visual signal, an auditory signal, or a tactile signal in US Patent Application Number 20130041617. A second sensor may be an accelerometer, a pressure sensor, a force sensor, a temperature sensor, a chemical sensor, a global positioning system, a piezoelectric sensor, a rotary position sensor, a gyroscopic sensor, a heart-rate sensor, and a goniometer.

Again, the measurement of the multiple factors of the walking pattern on the sole of the foot—body weight, center of body mass over the foot, number of steps in the gait cycle, cadence (speed of walking), and/or linear distance—is more effective than different factors.

An insole with a vibrating device is described in U.S. Pat. No. 8,844,166. The vibrating device stimulates circulation of the blood in the foot to prevent accumulation of blood in the foot and to warm the foot. The device does not have a haptic device or a smart phone app and is not intended for walking rehabilitation of the leg.

Another patent is for an insole outfitted with pressure sensors that provide biofeedback to a patient for gait therapy in U.S. Pat. No. 7,191,644. This system does not provide the feedback to a mobile app for real-time adjustments.

A system provides gait analysis of a walking person in US Pending Patent Application 2015/0257679. However, that system does not provide real-time feedback nor a feedback display.

A mobile terminal wirelessly communicates with foot sensors in U.S. Pat. No. 9,565,286. However, that device does not have a haptic device. nor an audio, visual and/or vibration feedback display.

Developing a device to assist walking rehabilitation is a difficult task because walking is such a complex process that is dependent on neurological feedback informing nuanced muscular responses. A system that assists walking rehabilitation must meet this inherent complexity. This complexity must be delivered by a solution that is person friendly, reliable, and durable.

The present invention is unique in that it identifies deviations from an ideal pressure distribution and provides feedback in real-time. Real-time feedback enables the patient to make the necessary adjustments for each step taken, simultaneously learning what a natural step feels like. The present invention will be used by the stroke victim at home, enabling the person to put in the necessary amount of time required to relearn to walk. Currently, stroke victims take years of physical therapy to make marginal gains, merely because the realistic frequency of physical therapy sessions does not provide enough repetitions.

There is currently no cost effective, user-friendly, product on the market to facilitate at-home walking rehabilitation. Additionally, no product on the market combines our intended methods of feedback into one app-centered solution.

It is an object of this invention to provide a passive foot sensor insole feedback device in a shoe insole to allow a person to improve their walking pattern in real-time.

SUMMARY OF THE INVENTION

According to the present invention, a feedback device determines when a person has placed enough weight upon his/her foot to safely take the next step, and then communicate that information to the person via a haptic device on the person's ankle and/or an audio, visual and/or vibration feedback display on an application on the person's smart phone to provide balance to a person while standing still or walking.

Three or more foot sensors are in an insole adjacent to the person's foot. The foot and the insole are in a shoe. The three or more sensors in an insole are between the person's shoe and foot determine the force of the person's foot. The force data is sent to a microprocessor where the force data is processed and compared with a baseline. If the processed data exceeds the baseline, the microprocessor will activate the haptic device on the person's ankle to vibrate and/or transmit the processed data through a wireless communications device to an application on a smart phone to activate an audio, visual and/or vibration feedback display on the application. The person will then safely take the next step.

Three or more foot sensors measure the force exerted by the foot on the insole while the person is walking on that leg and then send force data signals to the microprocessor in the data analysis and haptic response unit on the person's ankle or leg. The data analysis and haptic unit contains a microprocessor, a haptic device, and a wireless communications device.

The sensors are piezoresistive variable resistors, which act as force sensors when the person applies force to the insole.

The insole has three layers: an upper layer, a lower layer and an intermediate layer (between the upper layer and the lower layer) with openings in the intermediate layer to position each of the sensors and for a common channel to position the wires from the sensors through the insole in the foot to the microprocessor in the data analysis and haptic unit on the person's ankle or leg.

Three force sensors in the insole will be positioned under the heel, the mid foot and the fore foot.

Five force sensors in the insole will be positioned under the heel, the fifth metatarsal head, the first metatarsal head, the space between the second metatarsal head and the third metatarsal head, and the hallux (big toe).

The force sensors will interface with the microprocessor to provide force readings of the person's foot, which will be used to determine if the microprocessor should trigger the haptic device. The microprocessor will also send data through the wireless communications device to an app on a smart phone.

Each sensor of the multiple sensors sends a force data signal to the microprocessor. The microprocessor will compare each force data signal against a baseline for that force sensor. The microprocessor can be configured via the smartphone app to enable or disable sensing from each force sensor and to either OR or AND the results of a comparison of each enabled force data signal against its baseline to create a trigger event. In response to a trigger event, the microprocessor will activate the haptic device on the person's ankle to vibrate and/or transmit the processed data through a wireless communications device to an application on a smart phone to activate an audio, visual and/or vibration feedback display, based upon the person's preference, on the application. The person will then safely take the next step.

A plastic housing will secure and protect the microprocessor, the haptic device, the wireless communications device, and a rechargeable battery of the feedback device. The housing is attached by a strap to the person's ankle or leg.

The rechargeable battery provides power for the microprocessor, the haptic device, and the wireless communications device.

The haptic device will be any vibration motor to cause the housing on the person's ankle or leg to vibrate so that the person can feel the vibration at the ankle or leg, such as a Parallax 28822 or its functional equivalent.

The wireless communications device can be a Bluetooth or Bluetooth Low Energy or its functional equivalent.

The rechargeable battery can be any battery sufficient to power the microprocessor, the haptic device and the wireless communications device for at least one hour of constant use, which is also rechargeable, such as a lithium polymer battery or its functional equivalent.

The smart phone can run Android, IOS, or any smart phone operating system that supports Bluetooth Low Energy or its functional equivalent.

The app will log distance (ft.), time (s), and cadence (step/min) from each therapy session.

At the end of each therapy session, the app will store data concerning the duration of the session and number of steps taken.

Prior to operation of the feedback device of the present invention, the microprocessor under instructions from the smart phone app will calibrate the force sensors for the person to establish a baseline (a pressure distribution for the target foot that allows the person to take a step with the other foot).

To calibrate the feedback device, a physical therapist will position the person on the insole in a manner deemed to be the baseline. Through the application, the physical therapist will signal the microprocessor to enter "calibration" mode. During this time, the force sensors will take readings from each individual sensor over a five second period. The data will be averaged for each sensor. The average for each sensor will be stored as the baseline.

The application in the smart phone will have three main subsections: personal preferences, therapy session, and data view.

The first subsection is personal preferences; the person inputs their average step length and whether the target foot is the left foot or the right foot.

The person will enable or disable the force sensors, set a baseline for each enabled force sensor, and configure whether the results of comparing each enabled force sensor to its baseline shall be OR'd together or AND'd together to determine a trigger event.

The person will also have options for audio, vibratory, and/or visual feedback through the app on the smart phone for the feedback device of the present invention.

With audio feedback, the person will choose whether they want (1) a voice from the smart phone to alert them to take a step upon a trigger event or (2) a repetitive beeping sound from the smart phone that incrementally gets louder/faster as more weight is loaded.

Vibratory feedback is another option for the smart phone app. The smart phone will vibrate upon a trigger event. Again a visual alert on the screen of the smart phone will prompt the person to take a step.

Lastly, a visual feedback on the screen of the smart phone provides a visual representation of the weight distribution.

After the person selects their preferences, the person may enter the therapy session subsection. In this subsection, the person will have the option to begin a workout. The microprocessor will start taking data. Once the session has begun, a timer will act as a stopwatch and record the session time. The person will have the option to pause or end the workout at any time. Once the person ends the workout, the screen of the smart phone will display the time, distance, and average cadence over the session.

This data view subsection is meant to be motivational, as well as informative for the physical therapist and the person. After each session, the workout data will save into the database, thus keeping record of every completed workout.

Other aspects of the invention will become apparent from the following more detailed description, taken in conjunction with the accompanying drawings.

BRIEF DESCRIPTION OF THE DRAWINGS

The preferred embodiments of this invention will be described in detail, with reference to the following figures wherein.

DETAILED DESCRIPTION OF PREFERRED EMBODIMENTS

The feedback device of the present invention determines when a person has placed enough weight upon his/her foot in order to safely take the next step, and then communicate that information to the person via a haptic device on the person's ankle or leg and/or an audio, visual and/or vibration feedback display on an application on the person's smart phone.

Figure 1:
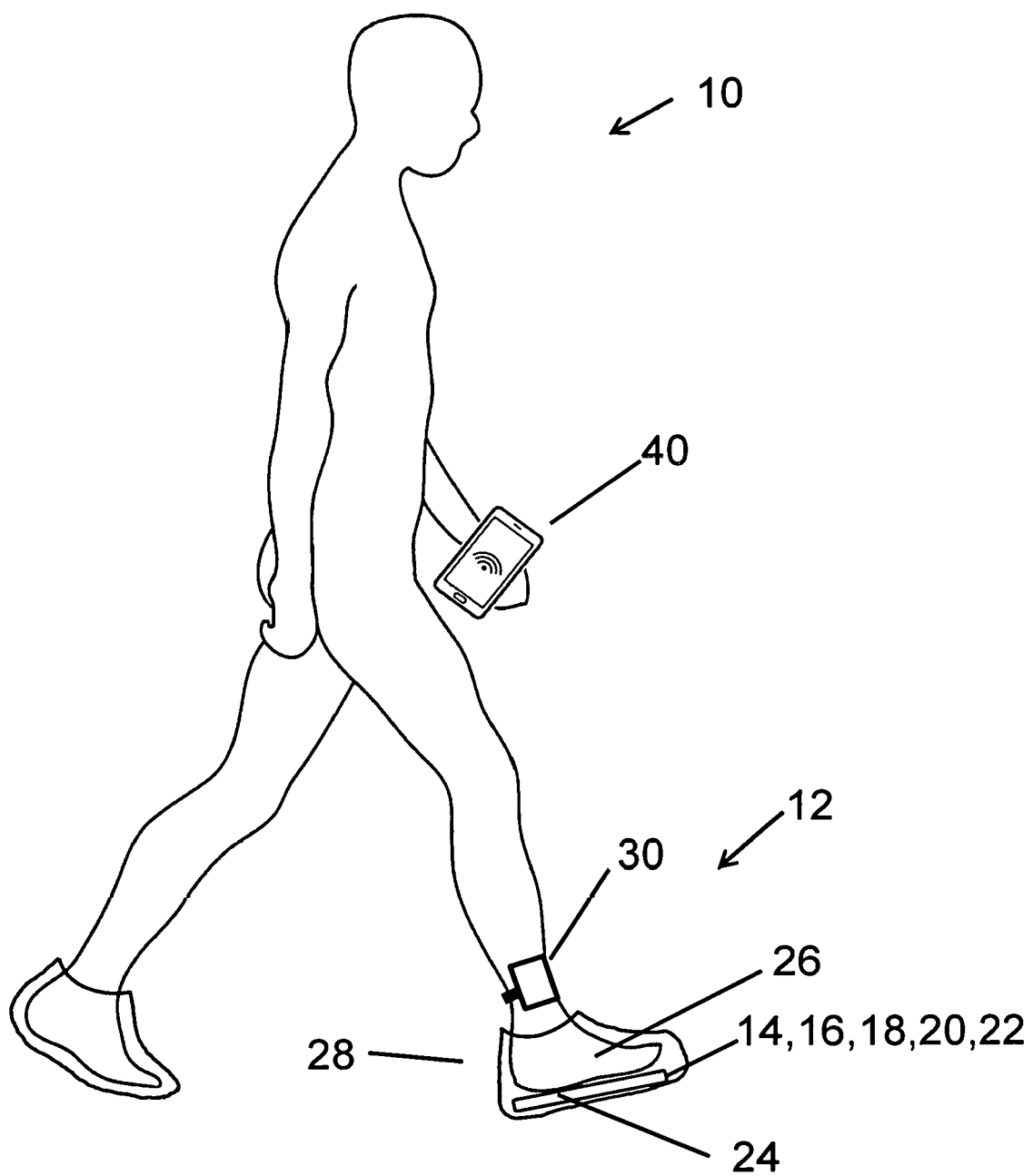
FIG. 1 is a side view of a walking person using the passive foot sensor feedback device of the present invention.

Reference is now made to FIG. 1, 3 illustrating a walking person 10 using the real-time passive foot sensor insole feedback device 12 of the first embodiment of the present invention. The feedback device 12 has multiple foot sensors 14, 16, 18, 20 and 22 in an insole 24 adjacent to the person's foot 26. The foot and the insole are in a shoe 28. Multiple sensors for the purposes of the present application are three or more sensors. The present embodiment presents a five sensor feedback device. A later embodiment presents a three sensor feedback device.

The sensors measure the force exerted by the foot on the insole while the person is walking on that leg and then send force data signals to the microprocessor in the data analysis and haptic response unit 30 on the person's ankle.

Figure 2:
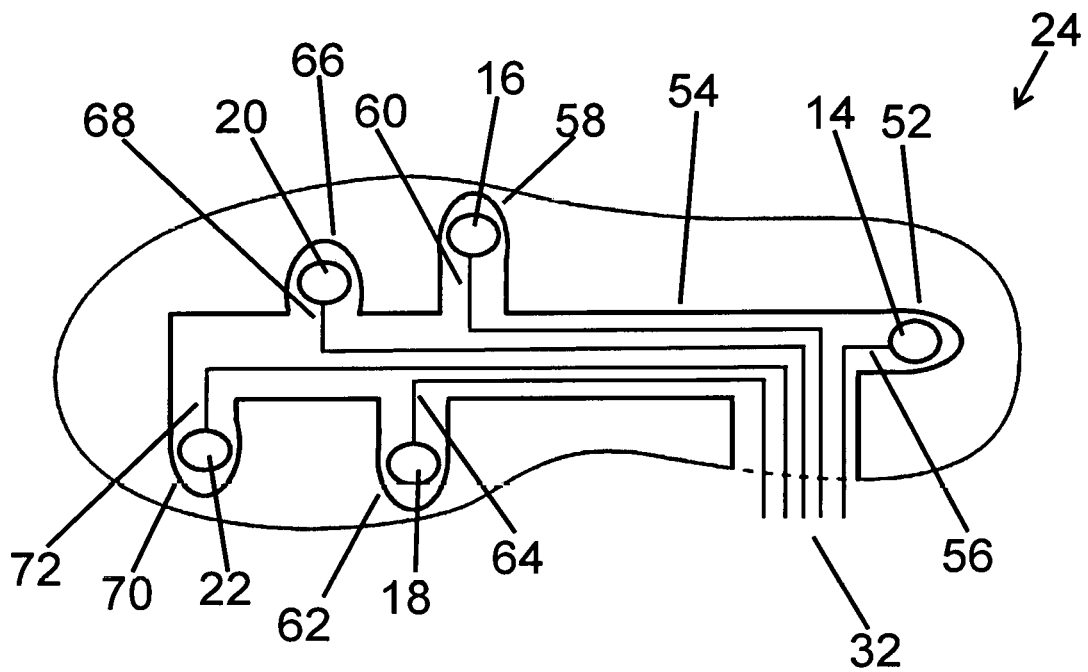
FIG. 2 is a top view of the five foot sensors in the shoe insole of the present invention.
Figure 3:
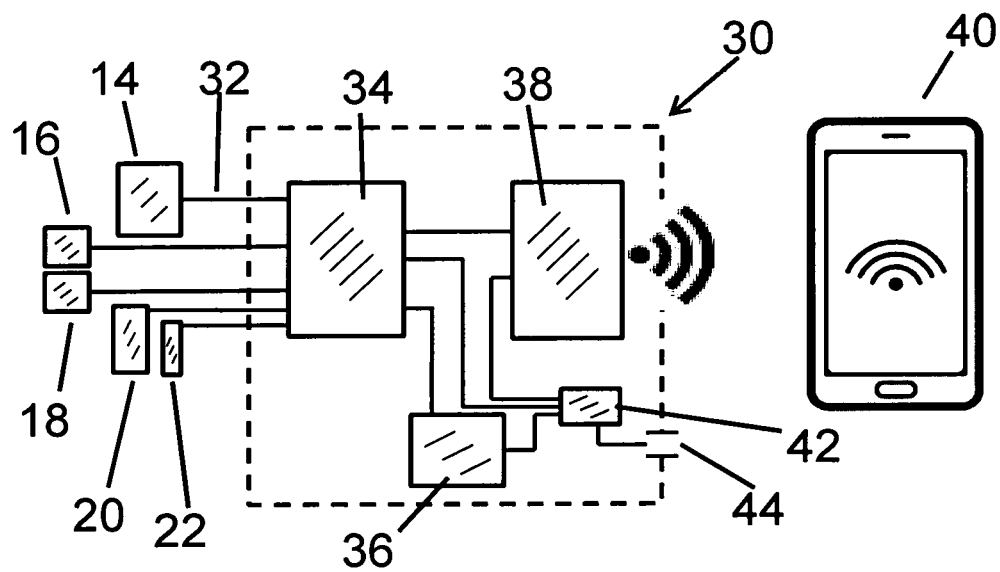
FIG. 3 is a top view of the housing and the data analysis and haptic response unit and rechargeable battery with an external smartphone of the present invention.

As shown in FIG. 2 and FIG. 3, the sensors in the insole 24 are connected by wires 32 to the microprocessor 34 in the data analysis and haptic response unit 30. The sensors in the insole of the foot are on the same leg as the data analysis and haptic response unit on the ankle.

The data analysis and haptic response unit 30 has three basic elements: a microprocessor 34, a haptic device 36, and a wireless communications device 38.

The microprocessor receives the forces data signals from the sensors in the insole and processes the data signals to form an average force data.

Each sensor of the multiple sensors sends a force data signal to the microprocessor. The microprocessor will compare each force data signal against a baseline for that force sensor. The microprocessor can be configured via the smartphone app to enable or disable sensing from each force sensor and to either OR or AND the results of a comparison of each enabled force data signal against its baseline. For example, force sensors 1, 3, and 5 could be enabled, each could have a different baseline, and the OR configuration could be set, so that if force sensor 1 exceeds its baseline OR force sensor 3 exceeds its baseline OR force sensor 5 exceeds its baseline, then a trigger event occurs. For another example, force sensors 2, 3, and 4 could be enabled, each could have a different baseline, and the AND configuration could be set, so that if force sensor 2 exceeds its baseline AND force sensor 3 exceeds its baseline AND force sensor 4 exceeds its baseline, then a trigger event occurs.

In response to a trigger event, the microprocessor will activate the haptic device on the person's ankle to vibrate and/or transmit the processed data through a wireless communications device to an application on a smart phone to activate an audio, visual and/or vibration feedback display, based upon the person's preference, on the application. The person will then safely take the next step.

The processed data is also sent by the microprocessor 34 to the wireless communications device 38 to be transmitted wirelessly to a smart phone 40, as shown in FIG. 3 and FIG. 1.

An application on the smart phone will display the processed data as visual, audio or vibration feedback and store the processed data.

The vibration signal on the ankle or leg and the feedback display on the smart phone will indicate to the person enough weight has been placed upon his/her foot in order to safely take the next step.

Generally, the basic components of the feedback device of the present invention are: the multiple sensors in the insole, the microprocessor, the haptic device, the wireless communications device, a battery, and an application on a smart phone.

More specifically as shown in FIG. 2, multiple sensors are positioned inside the insole 24. In the present embodiment, there are five piezoresistive variable resistors 14, 16, 18, 20, 22, which act as force sensors when the person applies force to the insole. Piezoresistive material decrease in resistance as force is applied. The piezoresistive variable resistors suitable for the feedback device of the present invention can be Tekscan Flexiforce A301 sensors or its functional equivalent. The sensors can be piezoresistive variable resistors or its functional equivalents.

The battery 42 can be replaceable or rechargeable. The battery provides power for the microprocessor, the haptic device, and the wireless communications device.

The rechargeable battery can be a lithium polymer battery or its functional equivalent.

The housing 30 will have an external USB 44 port connected to the internal rechargeable battery. A micro-USB cable (not shown) using a standard USB charger will be connected into the external USB port to recharge the rechargeable battery.

The piezoresistive force sensors are passive and do not require power, but the sensors are connected to the microprocessor, which is powered by the battery. Alternate sensors may require power, which would be supplied by the battery.

Figure 4:
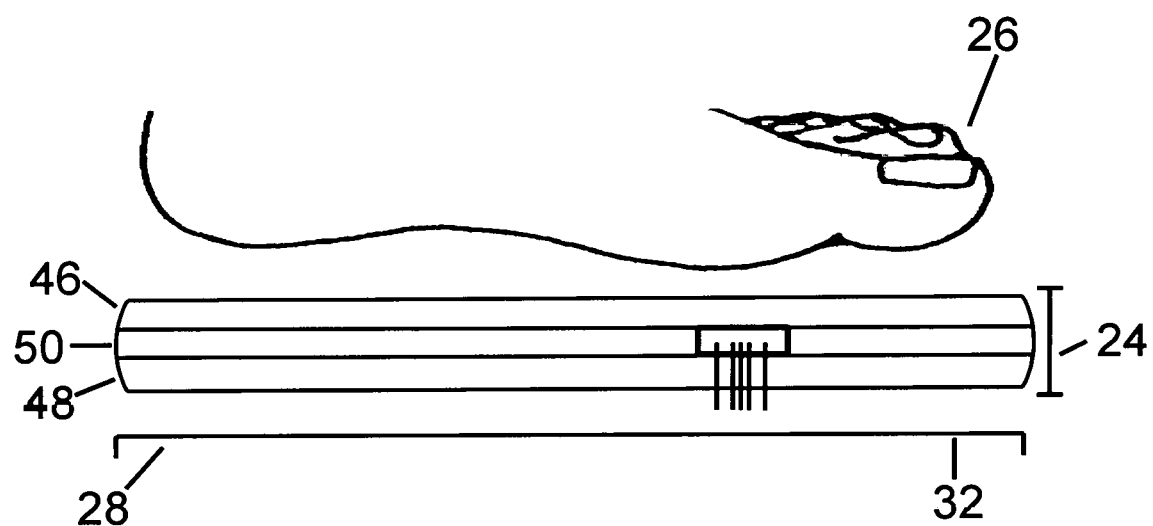
FIG. 4 is a side view of the three layers of the insole of the present invention.

As seen in FIG. 4 and FIG. 2, the insole 24 has three layers: an upper layer 46 adjacent to the foot 26, a lower layer 48 adjacent to the shoe 28, and an intermediate layer 50 between the upper layer and the lower layer.

The upper layer and the lower layer will be a flexible insole-shaped plastic or a flexible insole-shaped polymer. The intermediate layer will be a flexible insole-shaped plastic or a flexible insole-shaped polymer with openings 52 in the intermediate layer to position each of the sensors and a common channel 54 to position the wires 32 from the sensors through the insole in the foot to the microprocessor of the data analysis and haptic response unit at the ankle.

The openings and the channel in the intermediate layer can be formed during the molding of the intermediate layer. Alternately, the openings and the channel can be formed by cutting, etching, dissolving or other removal means into the intermediate layer.

The sensors will be thin and flexible with a circular force sensing area. The wires will also be thin and flexible.

The five force sensors in the insole will be positioned under specified areas of the foot: the heel, the fifth metatarsal head, the first metatarsal head, the space between the second metatarsal head and the third metatarsal head, and the hallux (big toe).

Accordingly, the first sensor 14 will be positioned under the heel in a first opening 52 in the intermediate layer of the insole. A first wire 56 attached to the first sensor will run from the first opening through a common channel and out the insole to the microprocessor. The first wire will carry force data signals transmitted from the first sensor to be received by the microprocessor.

The second sensor 16 will be positioned under the fifth metatarsal head in a second opening 58 in the intermediate layer of the insole. A second wire 60 attached to the second sensor will run from the second opening through the common channel and out the insole to the microprocessor. The second wire will carry force data signals transmitted from the second sensor to be received by the microprocessor.

The third sensor 18 will be positioned under the first metatarsal head in a third opening 62 in the intermediate layer of the insole. A third wire 64 attached to the third sensor will run from the third opening through the common channel and out the insole to the microprocessor. The third wire will carry force data signals transmitted from the third sensor to be received by the microprocessor.

The fourth sensor 20 will be positioned under the space between the second metatarsal head and the third metatarsal head in a fourth opening 66 in the intermediate layer of the insole. A fourth wire 68 attached to the fourth sensor will run from the fourth opening through the common channel and out the insole to the microprocessor. The fourth wire will carry force data signals transmitted from the fourth sensor to be received by the microprocessor.

The fifth sensor 22 will be positioned under the big toe in a fifth opening 70 in the intermediate layer of the insole. A fifth wire 72 attached to the fifth sensor will run from the fifth opening through the common channel and out the insole to the microprocessor. The fifth wire will carry force data signals transmitted from the fifth sensor to be received by the microprocessor.

The three layers will be bonded together with sensors and wires inside the intermediate layer to form the single insole. The insole will fit the contours of feet and the insides of shoes. The insole will also protect the sensors and wires from excessive shear, puncture, or extreme bending.

The sensor positions along the sole of the foot are based on the weight distribution on the foot for proper upright human posture during walking. The sensor positions can be adjusted based on the specific person and the weight distribution correction for walking.

The purpose of the insole is to safely house the multiple force sensors while maintaining the comfort and safety of the person. The insole with the sensors can be removed and used for several patients by a therapist or be removed and used by a person for multiple shoes.

A walking person will not feel the multiple sensors underfoot.

The person can wear a sock on his foot when the feedback device is being used. Socks are flexible and conform to the shape of the foot, thus they do not concentrate the forces of the foot any differently than the bare foot.

The force sensors interfaced with the microprocessor will provide force readings of the person's foot, which will be used to determine if the microprocessor should trigger the haptic device. The microprocessor will also send data through the wireless communications device to an app on a smart phone.

The force sensors used will be variable resistors, which will result in an analog voltage value that will be processed by the microprocessor. The microprocessor will determine if the haptic device should be triggered. The microprocessor will also communicate with the application through the wireless communications device. The force sensor data will be processed to determine if the person can take a step and will be sent to the application.

Figure 5:
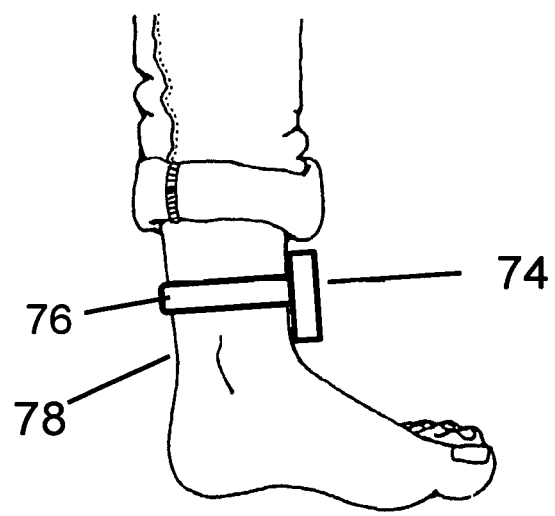
FIG. 5 is a side view of the housing and strap on the ankle of the person of the present invention.

A plastic housing 74 in FIG. 5 will secure and protect the microprocessor, the haptic device, the wireless communications device, and the rechargeable battery of the feedback device. The plastic housing will be small in size and weight. The housing, attached by a strap 76 to the person's ankle 78, will not affect the walking pattern of the person, nor effect the person's balance, nor effect the amount of force the person places on his/her foot and the insole.

The housing will prevent electrical interference between the microprocessor and the wireless communications.

The housing will prevent mechanical and physical interference from the vibration of the haptic device to the microprocessor and the wireless communications device.

The housing will use press fits or snap fits or other functional equivalents (not shown) to secure the microprocessor, the haptic device and the wireless communications device.

The housing should withstand a person's weight if stepped on or fallen on. The housing should provide ample protection to the microprocessor, the haptic device and the wireless communications device, both from impact, from particles and from water or moisture.

The rechargeable battery provides power for the microprocessor, the haptic device, and the wireless communications device.

The haptic device will be a vibration motor to cause the housing on the person's ankle to vibrate so that the person can feel the vibration at the ankle, such as a Parallax 28822 or its functional equivalent.

The wireless communications device can be a Bluetooth or Bluetooth Low Energy or its functional equivalent.

The rechargeable battery can be any battery sufficient to power the microprocessor, the haptic device and the wireless communications device for at least one hour of constant use, which is also rechargeable, such as a lithium polymer battery or its functional equivalent.

The smart phone can run Android, IOS, or any smart phone operating system that supports Bluetooth Low Energy or its functional equivalent.

Five force sensors will be used on the insole. The force sensors will be connected to the processor on a printed circuit assembly via a junction. This junction has 7 pins total, one in common that is connected to the microprocessor, and 6 others that are connected to ground through a MOSFET. The MOSFET's act as switches; the switch will remain open unless the microprocessor outputs a logic 1 to the GPIO port the MOSFET is connected to.

One end of each force sensor will be connected to the common pin, which is connected to an Op-Amp internal to the microprocessor. The other end of the force sensor will be connected to a junction pin. When a switch is closed, for example on J5, the force sensor can be read. The force sensor is a variable resistor, so when force is applied, its resistance decreases, causing a change in voltage of the output terminal of the Op-Amp. The output terminal of the Op-Amp is connected to the input terminal of the ADC internal to the microprocessor.

The app will log distance (ft.), time (s), and cadence (step/min) from each therapy session.

At the end of each therapy session, the app will store data concerning the duration of the session and number of steps taken.

The application will have a start button, which begins a timer for the duration of the workout. When the workout is finished, the app will sum how many times the haptic device was activated. The average step length (periodically determined by the physical therapist) will be saved as a value into the person's settings in the app. The distance will be determined by multiplying step length (×2) with number of steps. Cadence will be calculated as number of steps divided by total time. The person's preference for units, metric or will be determined in the settings.

The housing will have an external USB port connected to the internal rechargeable battery. A micro-USB cable will be plugged into the external USB port to recharge the rechargeable battery.

Prior to operation of the feedback device of the present invention, the microprocessor under instructions from the smart phone app will calibrate the force sensors for the person to establish a baseline (a pressure distribution for the target foot that allows the person to take a step with the other foot).

To calibrate the feedback device, a physical therapist will position the person on the insole in a manner deemed to be the baseline. Through the application, the physical therapist will signal the microprocessor to enter "calibration" mode. During this time, the force sensors will take readings from each individual sensor over a five second period. The data will be averaged for each sensor. The average for each sensor will be stored as the baseline.

The application in the smart phone will have three main subsections: personal preferences, therapy session, and data view.

The first subsection is personal preferences; the person inputs their average step length and whether the target foot is the left foot or the right foot.

The person will also have options for audio, vibratory, and/or visual feedback through the app on the smart phone for the feedback device of the present invention.

With audio feedback, the person will choose whether they want (1) a voice from the smart phone to alert them to take a step once the baseline is met or (2) a repetitive beeping sound from the smart phone that incrementally gets louder/faster as more weight is loaded. When the baseline is met, the beeping sound becomes continuous at full volume. Another option plays a high volume tone from the smart phone when the baseline is met. Each option of audio feedback will have a visual alert on the screen of the smart phone prompting the person to take a step, when the baseline is achieved.

Vibratory feedback is another option for the smart phone app. The smart phone will vibrate once the baseline is met. Again a visual alert on the screen of the smart phone will prompt the person to take a step.

Lastly, a visual feedback on the screen of the smart phone provides a visual representation of the weight distribution. Following the motion of a step, colored circles will occupy the screen; red meaning the patient has loaded a small portion of his/her weight, yellow indicating the patient is making progress but not quite ready to step, and green indicating that the patient has met the baseline and can step. The screen will again alert the person to take a step. Colored circles are merely an illustrative example, other shapes and patterns can be used.

After the person selects their preferences, the person may enter the therapy session subsection. In this subsection, the person will have the option to begin a workout. The microprocessor will start taking data. Once the session has begun, a timer will act as a stopwatch and record the session time. The person will have the option to pause or end the workout at any time. During the session, the microprocessor will keep track of how many times the haptic device at the ankle has activated, giving the person a rough estimate of how many steps they took. Once the person ends the workout, the screen of the smart phone will display the time, distance, and average cadence over the session.

This data view subsection is meant to be motivational, as well as informative for the physical therapist and the person. After each session, the workout data will save into the database, thus keeping record of every completed workout. The physical therapist can view this data in order to see the progress that the person has made or if the person has plateaued and needs to be pushed harder or softer given the circumstances. On the other hand, the person can view the data and see their progress, motivating them to work towards improvements.

Returning to FIG. 3, an alternate embodiment will have the same elements functioning the same process as the feedback device 12 except that the haptic device 36 has been removed from the feedback device 12. The only remaining feedback display for the feedback device would be the as visual, audio or vibration feedback display on the smartphone from the application.

Another alternate embodiment would will have the same elements functioning the same process as the feedback device 12 except that the microprocessor 34 has been removed from the feedback device 12. Each individual data signal from each individual sensor would be sent by wires 32 from the sensors directly to the wireless communications device 38 to be transmitted wirelessly to a smart phone 40, as shown in FIG. 3 and FIG. 1.

An application on the smart phone will process and display the individual data signals as visual, audio or vibration feedback and store the processed data. The application can also communicate wirelessly back through the wireless communications device 38. In response to a trigger event, the application will activate the haptic device on the person's ankle to vibrate In another alternate embodiment, the application may also receives the data signals from the sensors in the insole and processes the data signals to form an average force data. like the microprocessor did. In response to a trigger event, the microprocessor will activate the haptic device on the person's ankle to vibrate and/or transmit the processed data through a wireless communications device to an application on a smart phone to activate an audio, visual and/or vibration feedback display, based upon the person's preference, on the application. The person will then safely take the next step.

Still another embodiment would will have the same elements functioning the same process as the feedback device 12 except that the haptic device 36 and the microprocessor 34 have both been removed from the feedback device 12. The only remaining feedback display for the feedback device would be the as visual, audio or vibration feedback display on the smartphone from the application. Each individual data signal from each individual sensor would be sent by wires 32 from the sensors directly to the wireless communications device 38 to be transmitted wirelessly to a smart phone 40.

Figure 6:
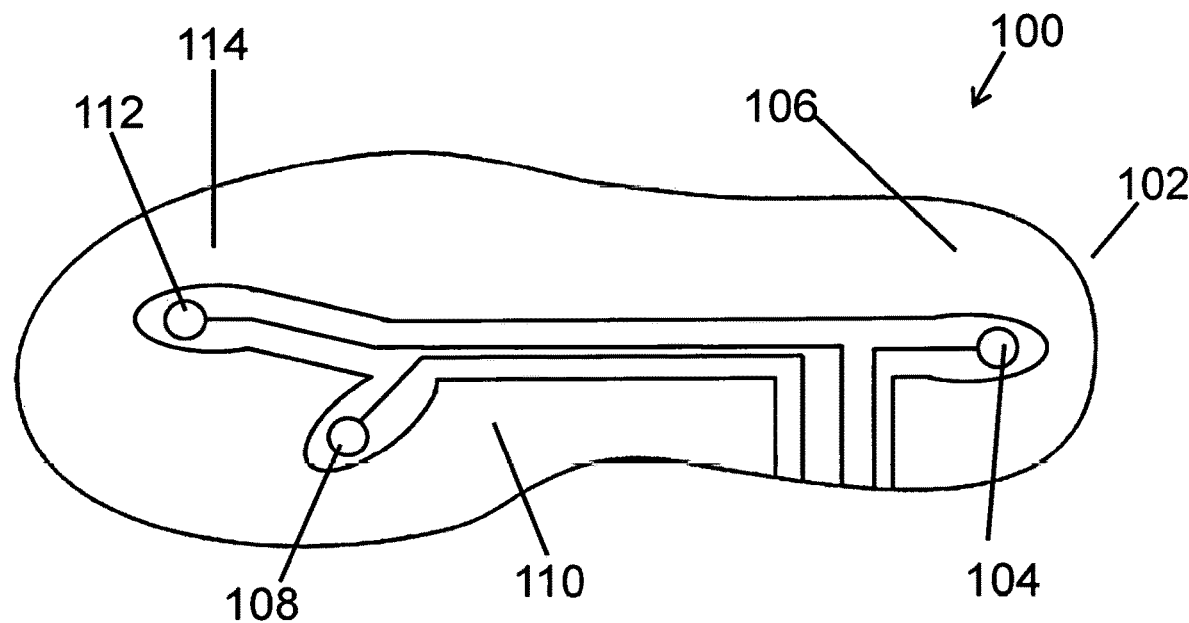
FIG. 6 is a top view of the three foot sensors in the shoe insole of the present invention.

Reference is now made to FIG. 6 illustrating the intermediate layer 102 of an insole of a three sensor feedback device 100. The first sensor 104 is at the heel 106, the second sensor 108 is at the mid foot 110, and the third sensor 112 is at the fore foot 114.

The feedback device for three sensors will have the same insole, the same microprocessor, the same haptic device, the same wireless communications device, and the same application on a smart phone as the feedback device for five sensors. The only distinctions will be the three sensors, the microprocessor processing only three data signals, and the smart phone app processing only three data signals from the microprocessor. The data signals from multiple sensors only change the number of data inputs to the microprocessor and the smart phone app.

The feedback device of the present invention can have alternate embodiments by providing functional equivalents or repositioning of the basic elements of: the sensors in the insole, the microprocessor, the haptic device, the wireless communications device and the app on the smart phone.

The first alternate embodiment would be the sensors, the microprocessor, and the haptic device all positioned in the insole. The sensors, the microprocessor, and the haptic device would be inside the arch of the insole, where there is the least amount of pressure from the foot. The sensors, the microprocessor, and the haptic device can be in a housing that would be able to withstand the pressure of the person's body weight.

The tactile feedback from the vibration motor of the haptic device will be on the sole of the foot making the feedback device more effective. The feedback device would be more compact in just one insole housing rather than spread across an insole and an ankle housing.

The second alternate embodiment has pressure sensitive textiles for the sensors in the insole and conductive fabric for the wires from the pressure sensitive textiles sensors to the microprocessors in the insole. This alternate keeps the microprocessor and the wireless communications device in an ankle housing and keeps smart app in the smartphone. The pressure sensitive textiles and conductive fabric can map the insole for a better map of the pressure of the foot.

A tactile transducer works similarly to a speaker, but directs vibrations into solid objects. The tactile transducer can be a miniature bass shaker. Depending on the amount of pressure placed on the insole, the tactile transducer would send out different frequencies. Frequency would increase with pressure. A wide range of frequencies can be accessed specifically. Additionally, bass shakers use strong vibrations that the person could potentially have an easier time feeling the vibration.

The third alternate embodiment would have the sensors, the microprocessor, the haptic device and the wireless communications device all positioned in the insole. The wireless communications device in the insole would have wireless capabilities beyond connection to a smartphone application, but it would also connect to other modules that contain a microprocessor, a haptic device and a wireless communications device.

These modules would be designed so that they could be placed anywhere on the person. They could be strapped to legs, arms, wrists, waists, canes, walkers, etc. The person would have the flexibility to choose where to receive haptic feedback in the event certain body locations lack the sensitivity needed to feel the feedback. Maximum vibratory feedback can be sent up the leg by covering as much surface area as possible. With more vibration, the person would ideally have a higher chance of connecting the vibration sensation with walking. The person's preference would also be taken into account. If the person wanted more vibration, the person could add on a module; less vibration, remove a module.

An alternate design for the insole will have the sensors and the connecting wire positioned between the upper layer and lower layer, with no intermediate layer involved.

Figure 7:
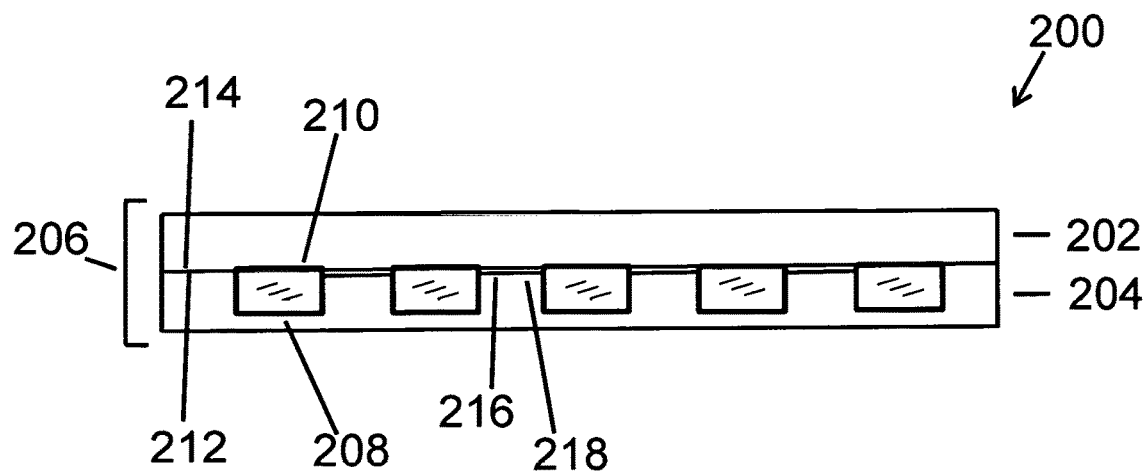
FIG. 7 is a side view of the two layers of the insole of the present invention.

The fourth alternate embodiment of the feedback device 200 of a two layer insole of FIG. 7 would have an upper layer 202 and a lower layer 204 to the insole 206. A recess 208 will be formed in the lower layer for positioning each sensor 210. A recess will be formed in the lower layer for positioning the connecting wires from each sensor to the microprocessor.

The sensor in the recess will be flush with the upper surface 212 of the lower layer and the lower surface 214 of the upper layer. The wire 216 in the channel recess 218 will be flush with the upper surface of the lower layer and the lower surface of the upper layer.

The remaining elements of the feedback device will be the same as the earlier embodiments: the positioning of the sensors, the microprocessor, the haptic device, the wireless communications device, the battery, and the app on the smartphone.

The upper layer and the lower layer will be a flexible insole-shaped plastic or a flexible insole-shaped polymer.

The openings and the channel in the lower layer can be formed during the molding of the lower layer. Alternately, the openings and the channel can be formed by cutting, etching, dissolving or other removal means into the lower layer.

The sensors will be thin and flexible with a circular force sensing area. The wires will also be thin and flexible.

The recesses for the sensors and the recess for the wire channel can alternately be formed in the bottom surface of the upper layer or in both the upper surface of the lower layer and the bottom surface of the upper layer.

Figure 8:
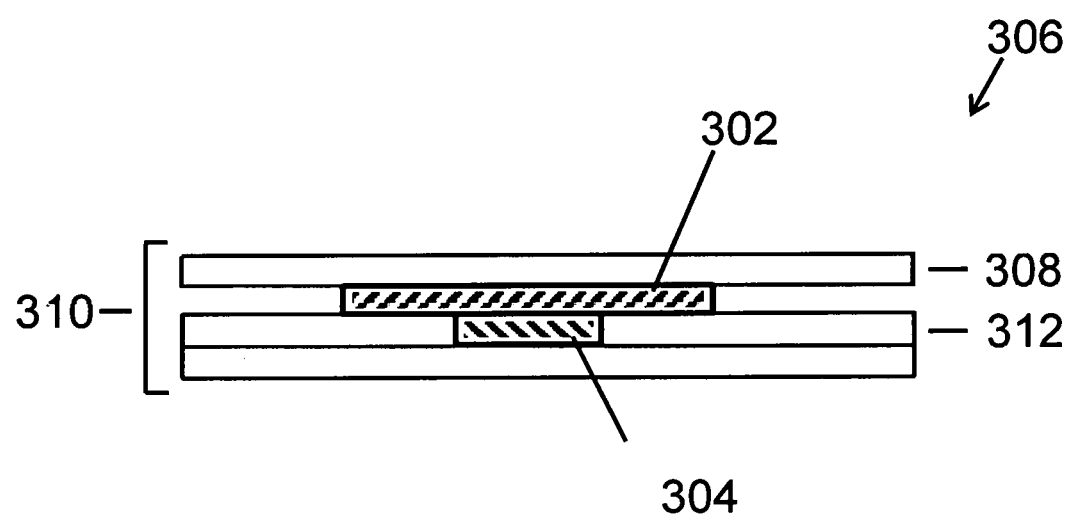
FIG. 8 is a side view of a force concentrator and the force sensor in the feedback device of the present invention.

The fifth alternate embodiment of the feedback derive of FIG. 8 has a force concentrator 302 in physical contact with the force sensor 304 in the feedback device 306. The force concentrator is adjacent and below the upper layer 308 of the insole 310 and adjacent and above the sensor in the opening of the intermediate layer 312.

Any load on the outside perimeter of the sensor is detrimental to the accuracy of force sensing.

The force concentrator is positioned over the force sensor. The force concentrator has a larger surface area than the force sensor.

The force concentrator will be used to increase the effective area of each sensor. The force concentrator will take a distributed load from the upper layer and focus the force down on the sensor.

The force concentrator is formed of plastic and is thin and inflexible. The force concentrator is thinner than the upper layer or the intermediate layer of the insole. It is more rigid than the upper layer or the intermediate layer of the insole.

The piezoresistive force sensors are only available in set circular diameters. The force concentrators can be a larger diameter circle or can be a shape that covers more of the weight of the foot on the insole, such as an oval, a square shape, a rectangular shape, a curved shape, or an irregular shape.

The force actuator/concentrator correspond to a larger area of the foot that apply the force from that area to the actual circular force sensors.

The feedback device of the present invention can be combined with a knee brace. The knee brace would have sensors to measure the angle of the brace when the person wearing the brace is walking. The insole next to the foot would be on the same leg as the knee and the knee brace. The knee brace sensors would send knee data signals to the microprocessor of the feedback device. The knee brace sensors would measure the angle of the bent knee to provide feedback concerning the person's gait. The knee system and insole system could work in conjunction to guide a properly applied pressure distribution in the foot in synchronization with the proper leg angle. This could help reinforce the complete motion associated with a natural gait, further improving posture when walking.

The haptic device of the present invention can be replaced with a sensory electrical stimulation device to indicate to the person that the person has placed enough weight upon his/her foot to safely take the next step.

The present invention can also provide balance training for the leg with the feedback device attached or both legs.

Balance is one of the key aspects of the rehabilitation device of the present invention. The person must be able to maintain the person's balance when standing still and also when taking steps to walk.

Static balance involves the person standing still on one foot or both feet. Dynamic balance involves the person moving one foot or moving both feet in sequence, one after the other. Static balance and dynamic balance are both important rehabilitation efforts.

The person has to have balance to place enough weight upon his/her foot to safely take the next step.

Balance is keeping the person's Center of Mass (COM) of the body over the Base of Support (BOS) (both feet or a single foot). The task of the feedback device is to constantly adjust the body's COM over the ever changing base of support (BOS).

The center of mass of a person's body typically located at ~S1 (Sacral vertebra 1) or the belt line of the person.

When walking, the balance on one leg allows the other leg to swing forward and the weight and balance of the person will shift to that other leg.

Balance through the feedback device allows the person to get to and stay on the ideal portion of the foot so the opposite foot can be advanced in any direction. Once the swing limb that moved, it touches the ground. That opposite foot is illuminated and the stance process on that foot continues.

As detailed earlier, once the force (weight) of the foot on the sensors reaches a baseline, the microprocessor will send a data signal to the application on the smartphone (via a wireless communications device) and the application will provide an audio, visual and/or vibration feedback display.

The application on the smartphone will have a balance point for the person based on the person's Center of Mass (COM) of the body over the Base of Support (BOS) and will have the person shift their weight to the balance point.

As the feedback device measures balance, a real-time feedback will occur as the person shifts their weight on the sensors and the microprocessor will send a newly updated data signal to the application on the smartphone (via a wireless communications device) and the application will alter the audio, visual and/or vibration feedback display. When the Center of Mass of the person's body approximately aligns with the Base of Support of the foot or feet of the person, the audio, visual and/or vibration feedback display will reach a maximum and the person can start walking from standing still or continue walking by shifting the person's weight to the other leg.

The feedback device for a person has an insole adjacent to the foot of said person; three or more force sensors in said insole for measuring the force of said person with each sensor generating a force data signal; a microprocessor for receiving each force data signal from each sensor and processing said force data signals and comparing said processed data signal against a baseline, a haptic device for generating vibrations to said person upon receipt of a signal from said microprocessor; said microprocessor sending such signal if said process data signal meets or exceeds the baseline, to indicate to said person that said person has placed enough weight upon his/her foot to safely take the next step, a wireless communications device; a smart phone, said microprocessor sending such signal if said process data signal meets or exceeds the baseline through said wireless communications device to said smart phone; and an application running on said smart phone, said application upon receipt of a signal from said microprocessor, generating a visual, audio, and/or vibration feedback display in said smart phone showing the alignment of the center of mass over the base of support of said person; said person shifts the person's force on said sensors to generate new data signals so that said microprocessor receives the new data signals and processes said new data signals to create a new signal to be sent through said wireless communications device to the application on said smartphone, said application upon receipt of a signal from said microprocessor, generating a new visual, audio, and/or vibration feedback display in said smart phone showing the new alignment of the center of mass over the base of support of said person; repeating until said center of mass is approximately aligned with the base of support of said person to indicate to said person that said person has placed enough weight upon his/her foot to safely take the next step.

Specifically, with an audio feedback display, the sound emitted by the smartphone will change from intermittent and low volume when the center of mass over the base of support is poorly aligned, to increasing constant tone and higher volume, as the person shifts their weight on the sensors to increase the alignment of the center of mass over the base of support and improve the person's balance. When the center of mass over the base of support are approximately aligned, the audio display can shift to another sound tone or have the smartphone vibrate or change the visual display.

Specifically, with a visual feedback display, the smartphone will show red when the center of mass over the base of support is poorly aligned, will show yellow as the person shifts their weight on the sensors to increase the alignment of the center of mass over the base of support and improve the person's balance. When the center of mass over the base of support are approximately aligned, the visual display will shift to green or the audio display will emit a sound tone or the vibration display will vibrate.

Specifically, with a vibration display, the vibration emitted by the smartphone will change from intermittent vibration and low speed of vibration when the center of mass over the base of support is poorly aligned, to increasing constant vibration and higher speed of vibration, as the person shifts their weight on the sensors to increase the alignment of the center of mass over the base of support and improve the person's balance. When the center of mass over the base of support are approximately aligned, the vibration display can shift to a different vibration or emit a sound tone or have the smartphone change the visual display.

Figure 9:
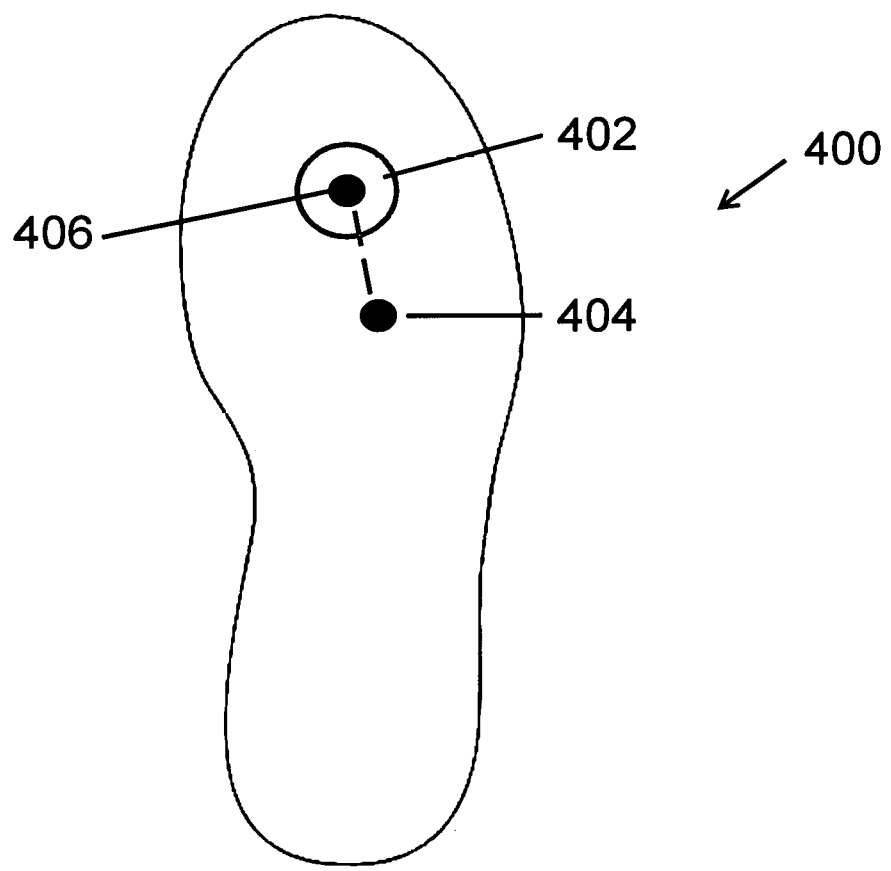
FIG. 9 is a top view of a position indicator and a target on the visual display of a smartphone of the present invention.

In a more advance visual display of FIG. 9, the application on the smartphone 400 will show a target 402 such as a target ring for the approximate alignment of the person's Center of Mass (COM) of the body over the Base of Support (BOS). A position indicator 404 such as a dot will show the person's actual alignment of the person's Center of Mass (COM) of the body over the Base of Support (BOS) as determined by the force (weight) of the foot on the sensors as processed by the microprocessor into data signal sent by the wireless communications device to the application on the smartphone.

As the person shifts their weight, in real-time, the position indicator will move closer or farther away from the target. Once the position indicator 406 is on top of the target 402, the center of mass over the base of support are approximately aligned.

The colors of the visual displays can be altered by the person or a third party for better visualization for the person.

A second insert in the other foot with a separate second sensors, a second microprocessor, a second haptic device, a second wireless communications device but a common application on the smart phone as the first insert (contralateral foot) provides the patient with comparative (control) data, for the purpose of matching the performance of the involved side with the control side.

Figure 10:
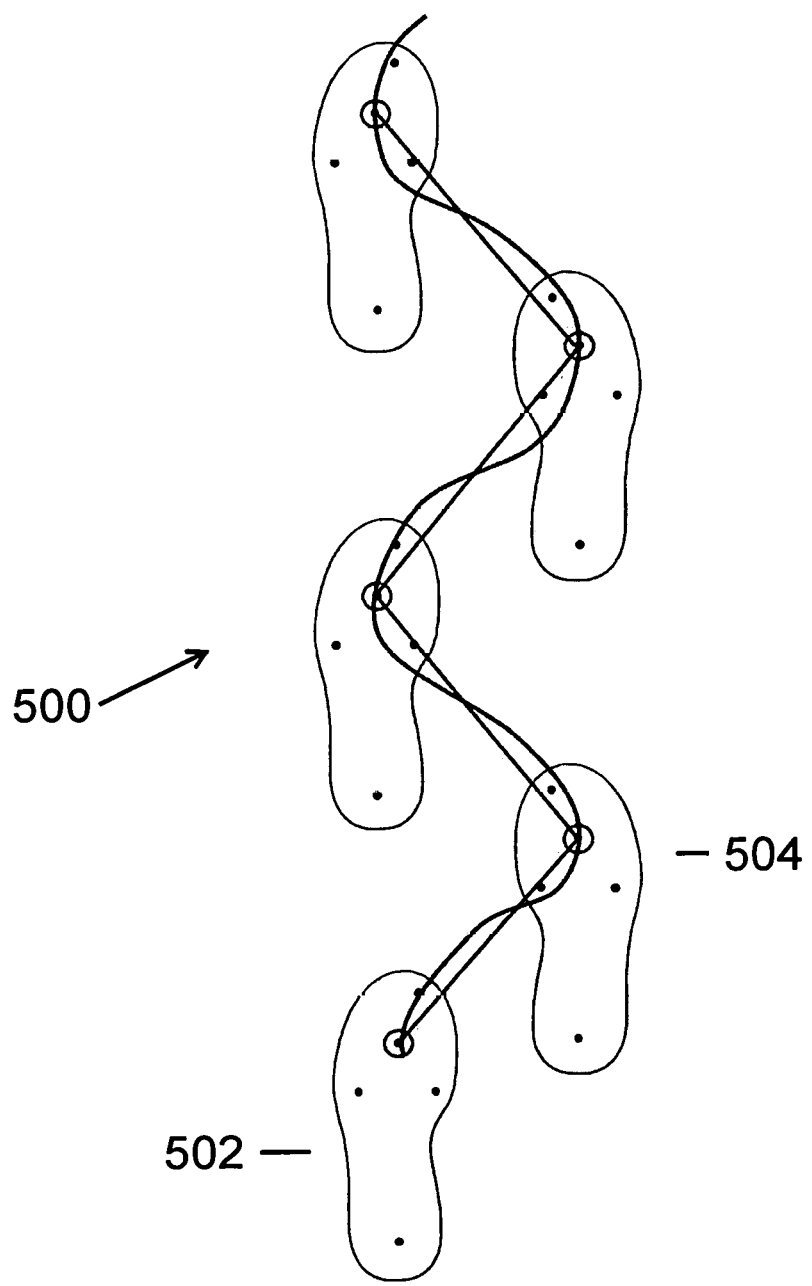
FIG. 10 is a top view of feet moving on the visual display of a smartphone of the present invention.

The visual display 500 of FIG. 10 shows two feet 502 and 504 offset to allow for a more realistic experience and it will scroll to give the appearance of walking. The COM moves in a predictable vector fashion which looks like a sinusoid wave or sine wave.

Scrolling of the feet on the visual display starts with the foot graphic side by side, then as the swing leg "zeros out", the foot graphic advances giving the appearance of taking a step or walking. Weight is transferred and as the now rear leg "zeros out". The "zeroed out" leg then advanced and the process repeats until the user stops walking. The foot graphic then resets to side by side (start) state. The position indicators are approximately aligned with the targets for each foot as the person walks.

A leg or knee brace can be used with the feedback device of the present invention to limit the forward and/or lateral motion of the leg to better assist in rehabilitation. The smartphone does not need to be handheld.

Figure 11:
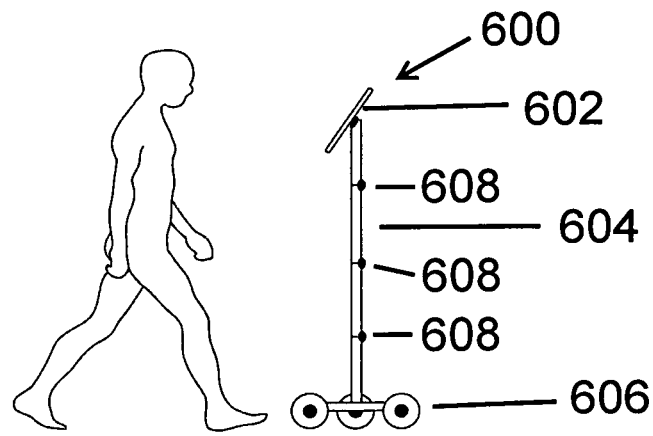
FIG. 11 is a side view of a person with a smartphone mounted on a rolling stand of the present invention.

The smartphone 600 of FIG. 11 can be mounted on an adjustable rolling stand 604. The vertical stand will have multiple wheels 606 at the bottom end for rolling the stand easily on the floor or other surface.

The top end of the stand will have a mount 602 to hold the smartphone in a position so that the display be viewed in real time by the person. The mount can be an adjustable swivel mount so the smartphone and its display will easily be viewed by the person regardless of the height of the person.

The vertical height of the stand can be a pole with one or more adjustable joints 608 in its stand to adjust the angle and height of the mounted smartphone relative to the person for ease of viewing. Alternately, the vertical height of the stand can be telescoping poles with a locking mechanism to adjust the angle and height of the mounted smartphone relative to the person for ease of viewing.

The adjustable rolling stand can be moved by the person or by a third party.

When the smartphone display is mounted separate from the hand of the person, then visual or audio displays are better for the feedback display to the person.

The adjustable rolling stand with mounted smartphone can be operated in a dynamic balance situation when the person is walking. The person can push the rolling stand ahead of the person while viewing the display in real time on the mounted smartphone. The person can adjust their balance on one foot then the other foot as the person walks.

The adjustable rolling stand with mounted smartphone can also be operated in a static balance situation when the person is standing still on one foot or standing still on both feet. The rolling stand will be stationary at a distance from the person so the person can the display in real time on the mounted smartphone.

The adjustable rolling stand with mounted smartphone can also be operated in static balance situation to adjust the alignment of the person's body in real time. The person can adjust the alignment of the person's legs, hips and upper body and view the display in real time. This real time alignment allows the person to determine the best available position of the person's legs, hips and upper body for static balance and dynamic balance for walking.

Figure 12:
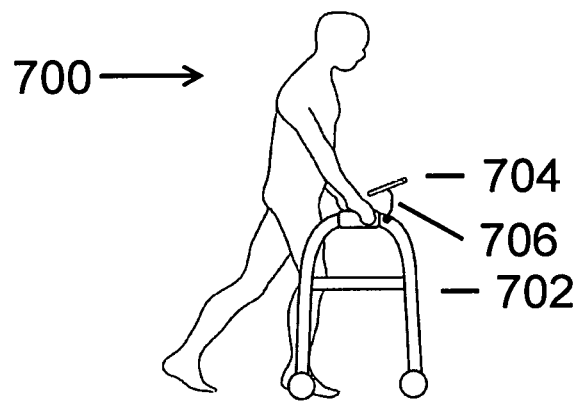
FIG. 12 is a side view of a person with a smartphone mounted on a walker of the present invention.

Alternately, the person 700 in FIG. 12 can hold onto a walker 702 as the person moves with the rehabilitation device. The smartphone 704 can be mounted 706 on an adjustable vertical stand from the front of the walker in a position to be viewed in real time by the person. The mount can be an adjustable swivel mount at the top of the stand, so the smartphone and its display will easily be viewed by the person regardless of the height of the person.

The vertical height of the stand can be a pole with one or more adjustable joints in its stand to adjust the angle and height of the mounted smartphone relative to the person for ease of viewing. Alternately, the vertical height of the stand can be telescoping poles with a locking mechanism to adjust the angle and height of the mounted smartphone relative to the person for ease of viewing.

The person will push or carry the walker and the mounted smartphone. The person can use one hand or both hands to push or carry the walker since the smartphone is mounted hands-free.

Weights can be added to the walker for additional stability of the walker when used by the person and for additional exercise of the legs of the person.

The walker and smartphone display can be operated when the person and the walker are stationary.

Figure 13:
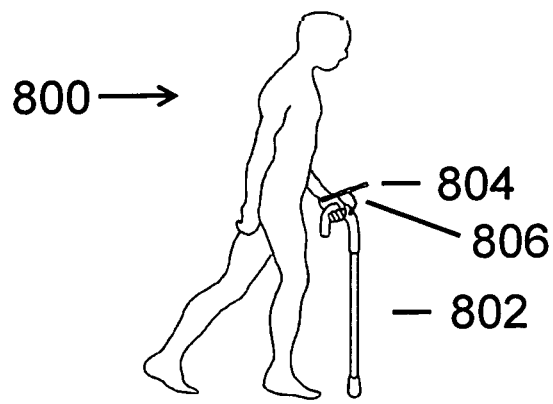
FIG. 13 is a side view of a person with a smartphone mounted on a cane of the present invention.

Again alternately, the person 800 in FIG. 13 can use a cane 802 or walking stick as the person moves with the rehabilitation device. The smartphone 804 can be mounted 806 on the top or side of the cane in a position to be viewed in real time by the person. The smartphone can be handheld in the same hand of the person gripping the cane or in the opposite (free) hand of the person from the cane.

The cane and smartphone display can be operated when the person and the cane are stationary.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention as defined in the following claims.

What is claimed is:

1. A feedback device for a person comprising:
an insole adjacent to a foot of said person;
three or more force sensors in said insole for measuring the force of said person with each sensor generating a force data signal:
a microprocessor for receiving each force data signal from each sensor and processing
said force data signals and comparing said processed data signal against a baseline;
a haptic device for generating vibrations to said person upon receipt of a signal from said microprocessor; said microprocessor sending such signal if said process data signal meets or exceeds the baseline;
a wireless communications device;
a smart phone, said microprocessor sending such signal if said process data signal meets or exceeds the baseline through said wireless communications device to said smart phone; and
an application running on said smart phone, said application upon receipt of a signal from said microprocessor, generating a visual, audio, and/or vibration feedback display in said smart phone showing an alignment of a center of mass over a base of support of said person;
said person shifts the person's force on said sensors to generate new data signals so that said microprocessor receives the new data signals and processes said new data signals to create a new signal to be sent through said wireless communications device to the application on said smartphone, said application upon receipt of the signal from said microprocessor, generating a new visual, audio, and/or vibration feedback display in said smart phone showing the new alignment of the center of mass over the base of support of said person; repeating until said center of mass is approximately aligned with the base of support of said person to indicate to said person that said person has placed enough weight upon his/her foot to safely take the next step, and wherein said microprocessor processes each force data signal from each sensor by averaging said force data signal to create the process data signal.

2. The feedback device of claim 1 wherein said three or more force sensors are three piezoresistive sensors in said insole.

3. The feedback device of claim 2 wherein said foot has a heel, mid foot and a fore foot, and wherein three piezoresistive sensors are positioned under the heel, the mid foot and the fore foot of said foot.

4. The feedback device of claim 1 wherein said three or more force sensors are five piezoresistive sensors in said insole.

5. The feedback device of claim 4 wherein said five piezoresistive sensors are positioned under the heel, the fifth metatarsal head, the first metatarsal head, the space between the second metatarsal head and the third metatarsal head, and the big toe of said foot.

6. The feedback device of claim 1 further comprising:
a battery for powering said microprocessor, said haptic device and said wireless communications device.

7. The feedback device of claim 1 wherein said wireless communications device is Bluetooth or Bluetooth Low Energy.

8. The feedback device of claim 1 further comprising:
a housing for securing said microprocessor, said haptic device, and said wireless communications device to an ankle of said person, said ankle being on the same leg as said foot of said person, said haptic device generating vibrations to said ankle of said person.

9. The feedback device of claim 1 wherein said haptic device is in said insole, said haptic device generating vibrations to said foot of said person.

10. The feedback device of claim 1 further comprising:
said insole having an upper layer adjacent to said foot, a lower layer adjacent to said shoe on said foot, and an intermediate layer between said upper layer and said lower layer; said intermediate layer having openings for each force sensor of said three or more force sensors.

11. The feedback device of claim 1 further comprising:
said insole having an upper layer adjacent to the foot and a lower layer adjacent to the shoe on said foot; said lower layer or said upper layer or both said upper layer and said lower layer having recesses for each force sensor of said three or more force sensors.

12. A feedback device for a person comprising:
an insole adjacent to a foot of said person:
three or more force sensors in said insole for measuring a force of said person with each sensor generating a force data signal;
a microprocessor for receiving each force data signal from each sensor and processing said force data signals and comparing said processed data signal against a baseline,
a haptic device for generating vibrations to said person upon receipt of a signal from said microprocessor: said microprocessor sending such signal if said process data signal meets or exceeds the baseline,
a wireless communications device;
a smart phone, said microprocessor sending such signal if said process data signal meets or exceeds the baseline through said wireless communications device to said smart phone; and
an application running on said smart phone, said application upon receipt of a signal from said microprocessor, generating a visual, audio, and/or vibration feedback display in said smart phone showing an alignment of a center of mass over a base of support of said person;
said person shifts the person's force on said sensors to generate new data signals so that said microprocessor receives the new data signals and processes said new data signals to create a new signal to be sent through said wireless communications device to the application on said smartphone, said application upon receipt of the signal from said microprocessor, generating a new visual, audio, and/or vibration feedback display in said smart phone showing the new alignment of the center of mass over the base of support of said person: repeating until said center of mass is approximately aligned with the base of support of said person to indicate to said person that said person has placed enough weight upon his/her foot to safely take the next step, and
a force concentrator adjacent to each force sensor of said three or more force sensors, said force concentrator having a larger surface area than said adjacent force sensor for increasing an effective area of each sensor for measuring the force of said person with each sensor generating the force data signal.

13. A feedback device for a person comprising:
an insole adjacent to a foot of said person;
three or more force sensors in said insole for measuring a force of said person with each sensor generating a force data signal;
a microprocessor for receiving each force data signal from each sensor and processing said force data signals and comparing said processed data signal against a baseline, a wireless communications device;
a smart phone, said microprocessor sending such signal if said process data signal meets or exceeds the baseline through said wireless communications device to said smart phone; and
an application running on said smart phone, said application upon receipt of a signal from said microprocessor, generating a visual, audio, and/or vibration feedback display in said smart phone showing an alignment of a center of mass over a base of support of said person;
said person shifts the person's force on said sensors to generate new data signals so that said microprocessor receives the new data signals and processes said new data signals to create a new signal to be sent through said wireless communications device to the application on said smartphone, said application upon receipt of the signal from said microprocessor, generating a new visual, audio, and/or vibration feedback display in said smart phone showing the new alignment of the center of mass over the base of support of said person: repeating until said center of mass is approximately aligned with the base of support of said person to indicate to said person that said person has placed enough weight upon his/her foot to safely take the next step.

* * * * *